United States Patent [19]

Wallach et al.

[11] Patent Number: 5,160,669

[45] Date of Patent: * Nov. 3, 1992

[54] METHOD OF MAKING OIL FILLED PAUCILAMELLAR LIPID VESICLES

[75] Inventors: Donald F. H. Wallach, Hollis; Rajiv Mathur, Nashua, both of N.H.

[73] Assignee: Micro Vesicular Systems, Inc., Nashua, N.H.

[ * ] Notice: The portion of the term of this patent subsequent to May 28, 2008 has been disclaimed.

[21] Appl. No.: 598,120

[22] Filed: Oct. 16, 1990

Related U.S. Application Data

[60] Continuation-in-part of Ser. No. 410,650, Sep. 21, 1989, Pat. No. 5,019,174, which is a continuation-in-part of Ser. No. 157,571, Mar. 3, 1988, Pat. No. 4,911,928, and a continuation-in-part of Ser. No. 443,516, Nov. 29, 1989, which is a division of Ser. No. 157,571.

[51] Int. Cl.⁵ .................... A61K 9/127; B01J 13/20
[52] U.S. Cl. .................... 264/4.3; 424/450; 428/402.2
[58] Field of Search ............ 264/4.3; 428/402.2; 424/450; 436/829

[56] References Cited

U.S. PATENT DOCUMENTS

| | | | |
|---|---|---|---|
| 2,980,941 | 4/1961 | Miller | 15/506 |
| 3,528,925 | 9/1970 | Chapuis | 252/559 |
| 3,957,971 | 5/1976 | Oleniacz | 424/70 |
| 4,133,874 | 1/1979 | Miller et al. | 428/402.2 |
| 4,212,758 | 7/1980 | Shashkina et al. | 252/119 |
| 4,217,344 | 8/1980 | Vanlerberghe et al. | 424/60 |
| 4,241,046 | 12/1980 | Papahadjopoulos et al. | 424/450 |
| 4,247,411 | 1/1981 | Vanlerberghe et al. | 428/402.2 |
| 4,297,374 | 10/1981 | Wess | 514/777 |
| 4,348,329 | 9/1982 | Chapman | 260/463 |
| 4,356,167 | 10/1982 | Kelly | 424/450 |
| 4,377,567 | 3/1983 | Gebo | 424/1.1 |
| 4,485,054 | 11/1984 | Mezei et al. | 264/4.6 |
| 4,508,703 | 4/1985 | Redziniak et al. | 424/450 |
| 4,536,324 | 8/1985 | Fujiwara et al. | 252/311 |
| 4,551,288 | 11/1985 | Kelly | 264/4.6 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,670,185 | 6/1987 | Fujiwara et al. | 252/311 |
| 4,692,433 | 9/1987 | Hostetler et al. | 514/12 |
| 4,695,554 | 9/1987 | O'Connell et al. | 436/528 |
| 4,772,471 | 9/1988 | Vanlerberghe et al. | 424/450 |
| 4,814,270 | 3/1989 | Piran | 435/7 |
| 4,885,712 | 12/1989 | Bally et al. | 424/450 X |
| 4,911,928 | 3/1990 | Wallach | 424/450 |
| 4,942,038 | 7/1990 | Wallach | 424/450 |
| 5,019,174 | 5/1991 | Wallach | 424/450 X |

FOREIGN PATENT DOCUMENTS

| | | |
|---|---|---|
| 0032578 | 7/1984 | European Pat. Off. . |
| 3410602 | 9/1984 | Fed. Rep. of Germany . |
| 59-106423 | 6/1984 | Japan . |
| 61-207324 | 9/1986 | Japan . |
| 85/01440 | 4/1985 | PCT Int'l Appl. . |
| 1539625 | 1/1979 | United Kingdom . |
| 2078543A | 1/1982 | United Kingdom . |
| 2079179A | 1/1982 | United Kingdom . |
| 2147263A | 5/1985 | United Kingdom . |
| 2166107A | 4/1986 | United Kingdom . |

OTHER PUBLICATIONS

Bangham et al. (1965) J. Mol. Biol. 13:238-252.

(List continued on next page.)

*Primary Examiner*—Richard D. Lovering

[57] ABSTRACT

A new "cold-loading" technique for filling the amorphous central cavity of paucilamellar lipid vesicles with a water immiscible material has been developed. Preformed, substantially aqueous filled paucilamellar lipid vesicles are mixed with the water immiscible material to be encapsulated under intermediate mixing conditions, thereby replacing the aqueous solution with the water-immiscible solution. The "cold-loading" technique is particularly useful for encapsulation of volatiles and heat labile materials.

10 Claims, 3 Drawing Sheets

OTHER PUBLICATIONS

Gregoriadis (1976) The New England Journal of Medicine 295:704–710.

Szoka, Jr. et al. (1978) Proc. Natl. Acad. Sci. USA 75:4194–4198.

*Liposomes* (Ostro, ed.) 1983, Marcel Dekker, Inc. New York, pp. 246–249.

Philippot et al. (1983) Biochem. Biophys. Acta 734:137–143.

Ribier et al. (1984) Colloids and Surfaces 10:155–161.

Baillie et al. (1985) J. Pharm. Pharmacol. 37:863–868.

"Methodes de preparation des liposomes", Dousset et al. (Puisieux and Dellattre, Eds.) 1985, Techniques et Documentation La Voisier Paris, pp. 41–72.

"Les niosomes", Handiani-Vila et al. (Puisieux and Dellattre, Eds.) 1985, Techniques et Documentation La Voisier Paris, pp. 297–313.

Philippot et al. (1985) Biochem. Biophys. Acta 821:79–84.

"Problems technoloqiques poses par l'utilisation des liposomes comme vecteurs de substances medicamenteuses. Encapsulation, sterilsation, conservation", Puisieux et al. (Les Liposomes, Eds.) 1985, Techniques et Documentation La Voisier Paris, pp. 73–113.

Baillie et al. (1986) J. Pharm. Pharmacol. 38:502–505.

METHOD OF MAKING OIL FILLED PAUCILAMELLAR LIPID VESICLES

REFERENCE TO RELATED APPLICATIONS

This application is a continuation-in-part of U.S. patent application Ser. No. 410,650, filed Sep. 21, 1989 and now U.S. Pat. No. 5,019,174, entitled "Liposomal Cleaner," which is a continuation-in-part of Ser. No. 157,571, filed Mar. 3, 1988, now U.S. Pat. No. 4,911,928, issued Mar. 27, 1990, entitled "Paucilamellar Lipid Vesicles." This application is also a continuation-in-part of U.S. patent application Ser. No. 443,516, filed Nov. 29, 1989, also entitled "Paucilamellar Lipid Vesicles," which is a divisional of the aforementioned Ser. No. 157,571, now U.S. Pat. No. 4,911,928. The disclosures of all the above applications and patents are incorporated herein by reference.

BACKGROUND OF THE INVENTION

The present invention relates to a method of forming paucilamellar lipid vesicles which have amorphous central cavities substantially filled with a water immiscible material such as an oil. The invention is a "cold-loading" technique which allows incorporation of volatile and/or heat labile (heat degraded) materials which could not otherwise be incorporated into the vesicles.

U.S. Pat. No. 4,911,928 describes a "hot-loading" method of making paucilamellar lipid vesicles with water immiscible material substantially filling the amorphous central cavities. The lipid (and any oil or water immiscible material to be incorporated) is heated to an elevated temperature, e.g., a liquid or flowable form, so that it can be injected into an excess of an aqueous phase. This injection of the lipid into the aqueous phase causes the formation of small lipid micelles (probably spheroidal) which aggregate upon cooling with turbulent or shear mixing. The aggregated micelles fuse into vesicles with multiple bilayer shells surrounding a central, amorphous core. If an oil or a water immiscible material is also present, both lipid micelles and microemulsion oil droplets are formed. The microemulsion oil droplets act as nuclei about which the micelles aggregate, forming an oil-filled amorphous central cavity of the vesicle surrounded by the lipid bilayers. Preferably, a small amount of an indifferent surfactant is also included to stabilize the oil. The term "indifferent surfactant," as used herein, means a surfactant which will not form lipid vesicles but is able to emulsify the water immiscible materials to be encapsulated. Indifferent surfactants include most polyoxyethylene sorbitan ethers (Tweens), sodium dodecyl sulphate, and $C_{12}$–$C_{18}$ fatty acids and their salts such as sodium oleate. If an indifferent surfactant is not used, a portion of the wall-forming lipid is cannibalized to stabilize the oil.

Although the "hot-loading" method is effective for a large number of water immiscible materials, the method is not useful for a variety of important water immiscible materials which are too volatile or heat labile at the vesicle forming temperatures. If the "hot-loading" methods are tried for these thermolabile materials, the majority of the water immiscible material is volatilized, leaving only a small portion to be incorporated into the vesicle. These volatile materials include insecticides such as diethyltoluamide (DEET), certain perfumes and fragrances, flavor oils, as well as many other materials such as mineral spirits. Since some fragrances are mixtures, release of one part of the mixture can change the overall properties dramatically. Further, even certain non-volatiles are more easily introduced into the amorphous central cavities of vesicles using the present "cold-loading" technique than the "hot-loading" technique. For example, the cleaning agent d-limonene can be incorporated into vesicles at a relatively low concentration using "hot-loading" but a much higher concentration can be achieved using the "cold-loading" technique.

Accordingly, an object of the invention is to provide a method of "cold-loading" the amorphous central cavities of paucilamellar lipid vesicles with water immiscible materials.

Another objection of the invention is to provide a means of incorporating volatiles into paucilamellar lipid vesicles.

A further object of the invention is to provide a generalized means of loading lipid vesicles with oily or water immiscible material which can be used with phospholipid, ionic, and nonionic lipid materials.

Further objects and features of the invention will be apparent from the description and the Drawing.

SUMMARY OF THE INVENTION

The present invention features a method of "cold-loading" the amorphous central cavities of paucilamellar lipid vesicles with water immiscible materials. The method is particularly important for volatile materials which cannot be loaded in significant quantities into the central cavities of paucilamellar lipid vesicles using a "hot-loading" technique.

The method of the invention commences with the formation of paucilamellar lipid vesicles having substantially aqueous-filled amorphous central cavities. The vesicles may be made by any classic technique but the methods and materials disclosed in U.S. Pat. No. 4,911,928 are preferred. Briefly, these methods require the injection of a flowable lipid, with or without a small portion of oil, into an excess of an aqueous phase using shear mixing techniques. The term "shear mixing," as defined in the aforementioned U.S. Pat. No. 4,911,928, means that the flow of the phases is equivalent to a relative flow of about 5–50 m/s through a 1 mm orifice. The resulting vesicles have the amorphous central cavity filled with an aqueous solution, possibly with some oil included.

After formation of the substantially aqueous-filled paucilamellar lipid vesicles, they are mixed with the water immiscible material, e.g., an oil, most preferably a volatile oil, to be incorporated into the amorphous central cavity under intermediate mixing conditions. The term "intermediate mixing conditions" means mixing of the preformed vesicles and the water immiscible material at or near room temperature under gentle conditions such as vortexing or syringing. Although flow conditions which yield a shear similar to that used to form the paucilamellar lipid vesicles initially could be used, it is unnecessary and may, in fact, be counterproductive.

Following this procedure, the amorphous central cavity of the lipid vesicles is filled with the water immiscible material, displacing the aqueous solution. The water immiscible material may act as a carrier for materials which are soluble or dispersed in it. The paucilamellar lipid vesicles are then separated from any excess oil, e.g., by centrifugation. Preferably, an indifferent surfactant is used in the process to stabilize the water immiscible material. The indifferent surfactant is normally aqueous soluble and carried in an external aqueous phase but a water insoluble indifferent surfactant can be incorporated in the amorphous center or walls of the paucilamellar lipid vesicles before the intermediate mixing. Preferred indifferent surfactants are selected from the group consisting of sodium dodecyl sulphate, $C_{12}$–$C_{18}$ fatty acids, Tweens (polyoxyethylene sorbitan esters), and their salts, and mixtures thereof.

Although the preferred paucilamellar lipid vesicles of the invention have non-ionic materials such as polyoxyethylene fatty acid esters, Polyoxyethylene glycerol monostearate, polyoxyethylene steryl alcohols, and diethanolamides as the wall or bilayer forming lipid, other materials such as phospholipids, betaines, and other ionic or zwitterion materials may be used. The invention is particularly preferable for encapsulation of volatiles or heat labile materials which are not stable liquids at temperatures where the wall forming lipid is a liquid.

Further aspects and features of the invention will apparent from the following description.

DESCRIPTION OF THE INVENTION

The "cold-loading" method of the present invention is preferable to the "hot-loading" method where the material to be loaded into the amorphous central cavity of the vesicles is a volatile or heat labile water immiscible material. Further, even though the material to be incorporated in the central cavity may not be volatile, a higher concentration of the water immiscible material may be loaded using the methods of the present invention.

Figure 1A:
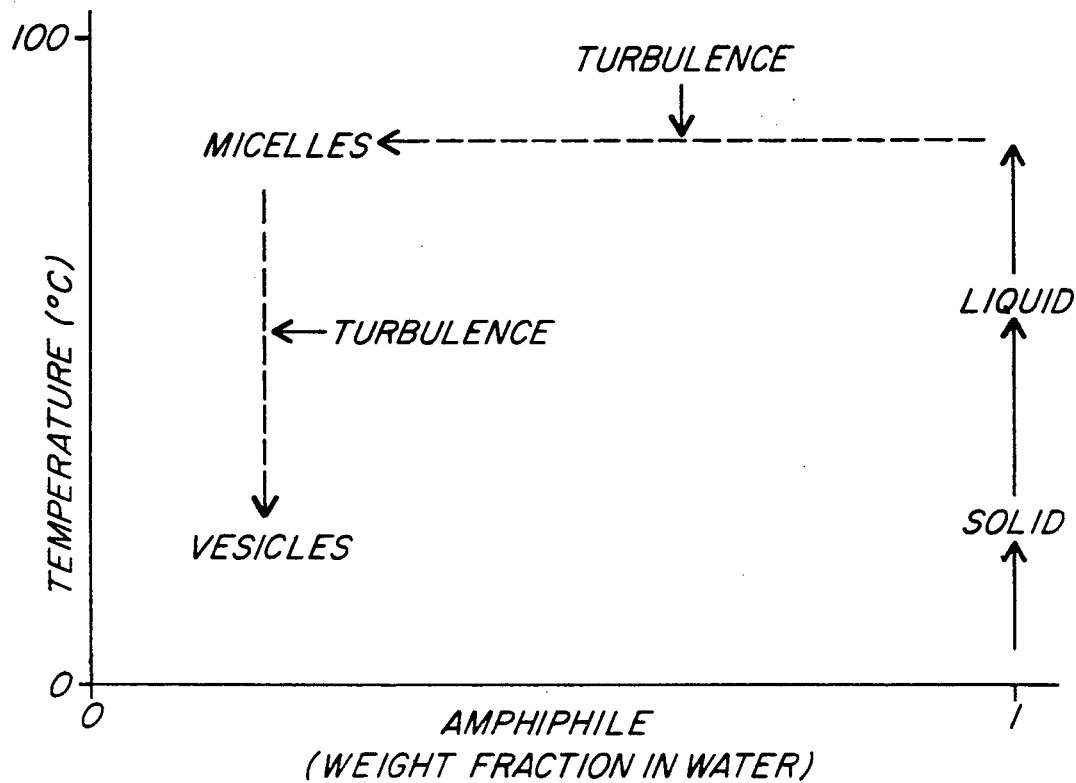
FIGS. 1a and 1b are illustrations of micelle formation upon injection of a lipid phase into an excess of aqueous phase such as is used in the "hot-loading" technique.
Figure 1B:
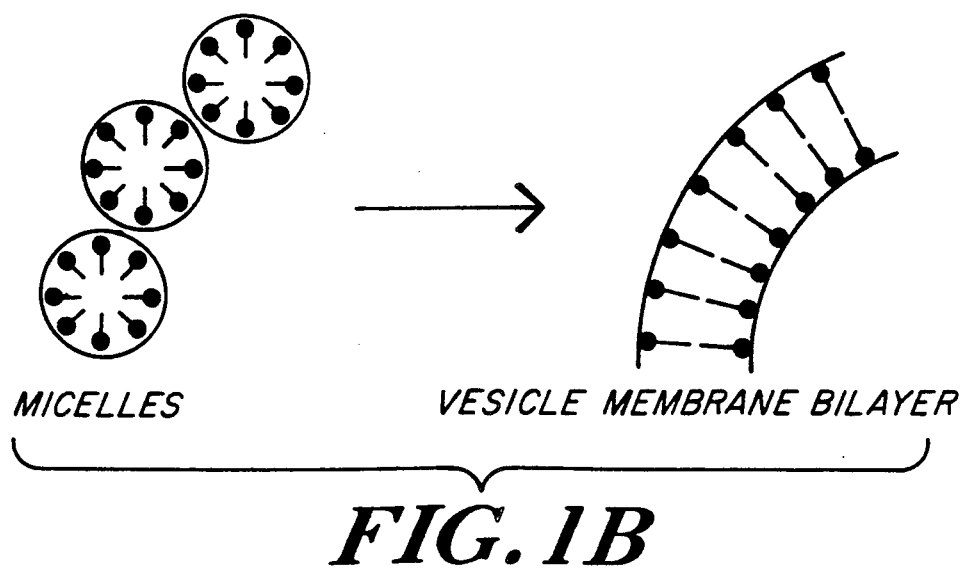

FIGS. 1a and 1b illustrate the critical step in the "hot-loading" technique without oil present, the formation of micelle structures by injection of the lipid phase into an excess of an aqueous solution. As noted previously, the micelles aggregate to form the bilayers of the paucilamellar lipid vesicle.

Figure 2A:
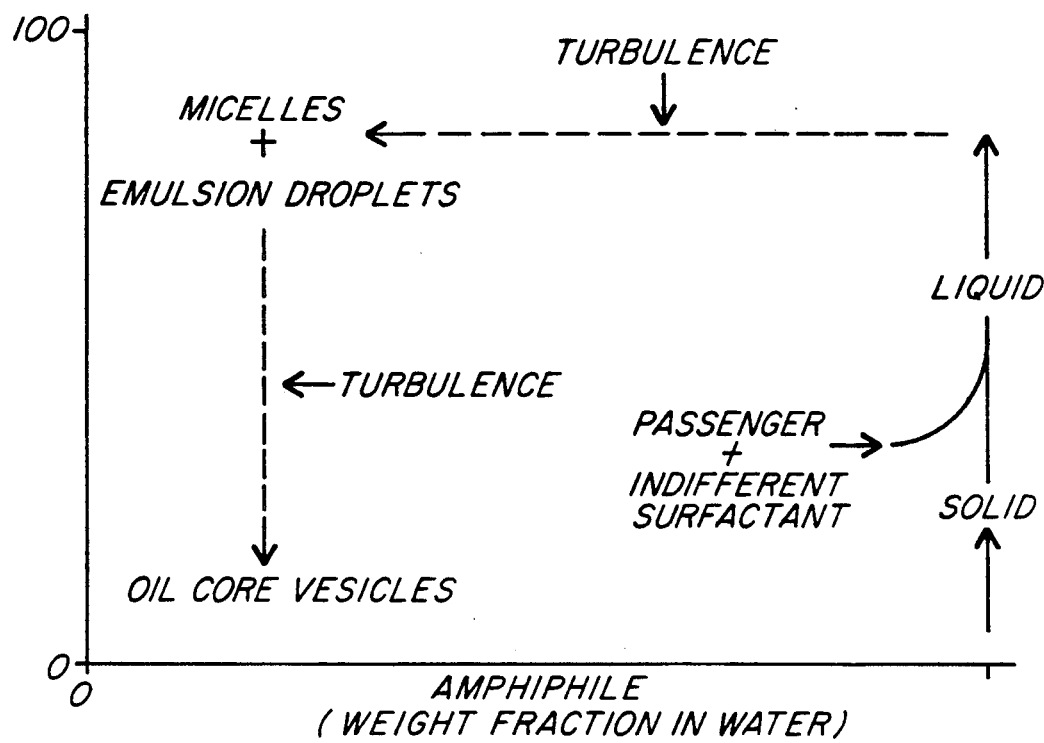
FIGS. 2a and 2b are illustrations of micelle and microemulsion formation upon injection of a lipid and water immiscible material phase into an excess of aqueous phase such as is used in the "hot-loading" technique.
Figure 2B:
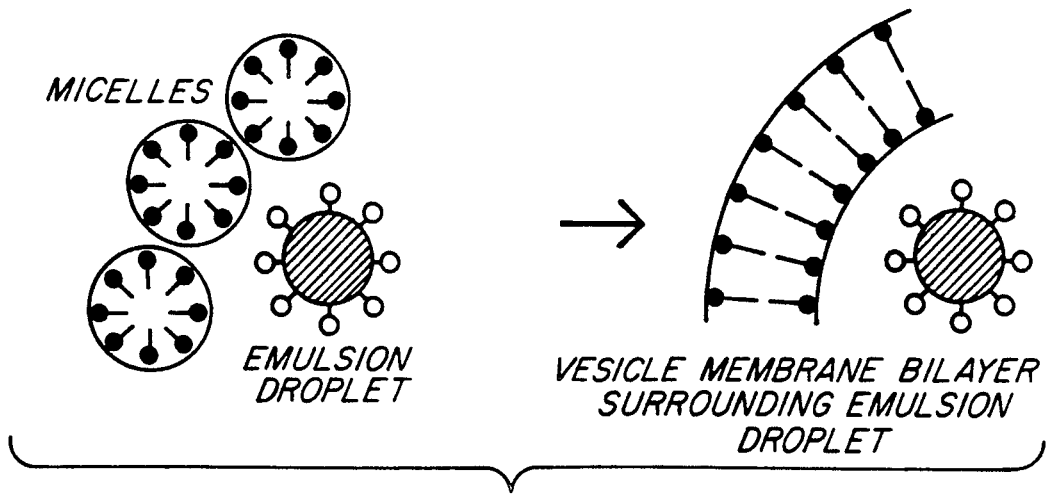

FIGS. 2a and 2b show the same mechanism with a water immiscible material added to the lipid. Both micelles and microemulsion oil droplets form. These microemulsion droplets are the nuclei about which the bilayers of the lipid vesicle form. Since these microemulsion oil droplets are necessary in this "hot-loading" technique, clearly a volatile material which will not form these microemulsions droplets are not appropriate for the "hot-loading" technique.

Figure 3:
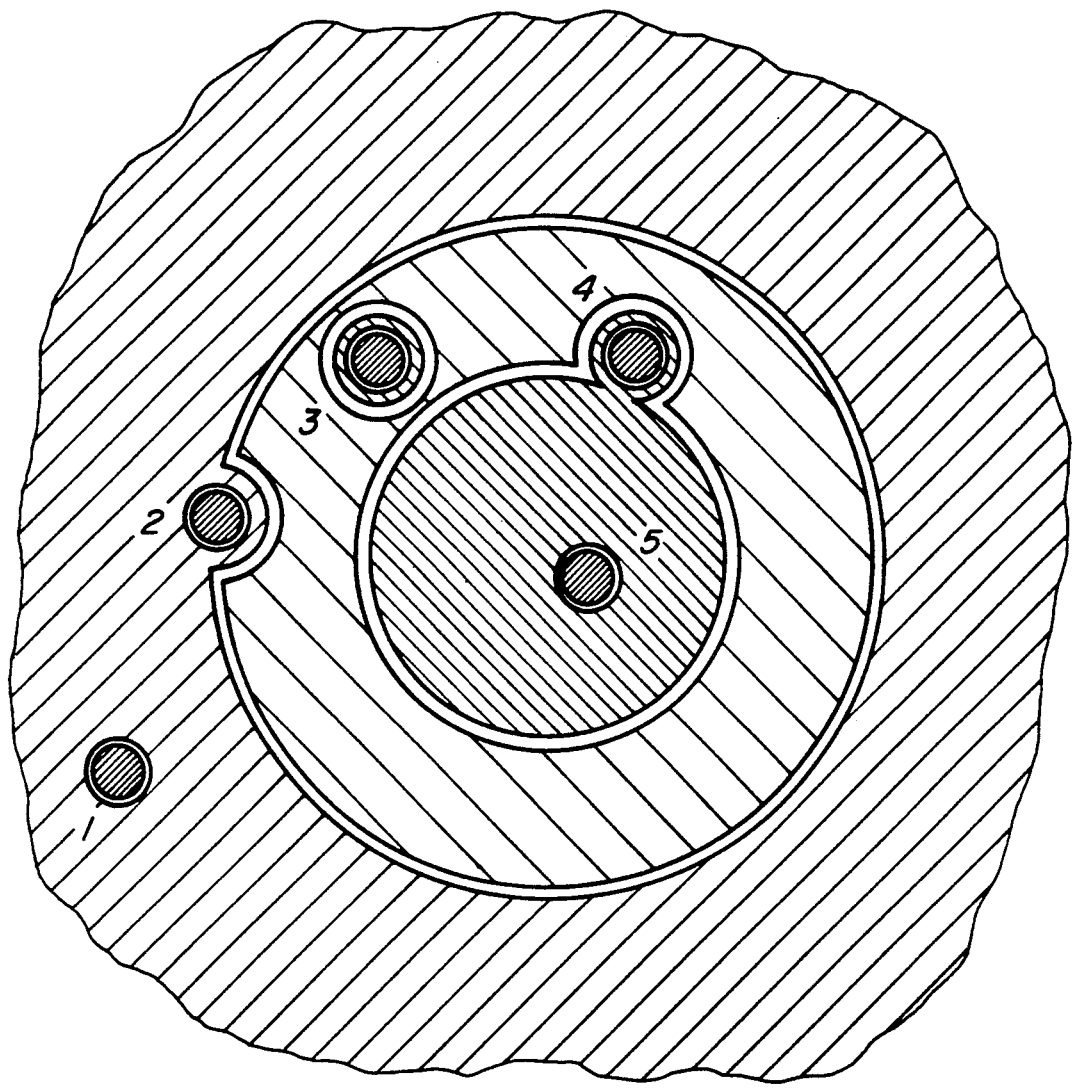
FIG. 3 is a schematic of the endocytosis mechanism suggested for the "cold-loading" technique of the present invention.

FIG. 3 illustrates the most likely mechanism of the "cold-loading" technique of the present invention. Once the substantially aqueous-filled paucilamellar lipid vesicles are formed, e.g., using the technique shown in FIG. 1, they are combined with the cargo material, e.g., the water immiscible material, preferably in the presence of a low concentration (approximately 1.5%) of an indifferent surfactant such as sodium dodecyl sulphate. Droplets of the water immiscible material (stabilized by the indifferent surfactant) enter the vesicles, presumably by a process resembling endocytosis.

Although the "cold-loading" technique is most preferred for volatile or thermolabile materials such as fragrance oils, flavor oils, and certain lipids or drugs, it is also particularly good for water immiscible materials which interfere with micelle formation and/or fusion. This latter group of materials includes diethyltoluamide, d-limonene, and certain water immiscible solvents such as petroleum distillates and aromatic solvents such as xylene. These materials, which cannot be encapsulated in lipid vesicles in any large quantity using the "hot-loading" techniques, can be incorporated in the amorphous central cavity of the paucilamellar lipid vesicles using the "cold-loading" technique of the present invention.

The following Examples will more clearly elucidate the present invention.

EXAMPLE 1

In this Example, aqueous-filled vesicles were made using the methods described in U.S. Pat. No. 4,911,928 from polyoxyethylene (9) glycerol monostearate, cholesterol, and a 1.5% solution of Tween 40 (polyoxyethylene 20 sorbitan monopalmitate). Briefly, the patent describes a technique whereby all of the lipid soluble materials (including any water immiscible materials if used), are blended together at elevated temperature until flowability. Normally, this requires a temperature of 60°–80° C. but in some cases as high as 90° C. The aqueous phase, which includes all the water soluble materials (including the indifferent surfactant, here the Tween), is also heated. The lipid phase in then injected into an excess of the aqueous phase through a moderate shear device and the mixture is sheared until vesicles form. While a device such as the mixing machine shown in U.S. Pat. No. 4,895,452, the disclosure of which is incorporated herein by reference, may be used, a pair of syringes connected by a three-way stopcock can provide shear sufficient for formation of the vesicles. The shear required is a relative flow of about 5–50 m/s through a 1 mm orifice. Further details of this process are described in U.S. Pat. No. 4,911,928. Table 1 lists the formula used to make the vesicles.

TABLE 1

| | |
|---|---|
| POE (9) glycerol monostearate | 20.3 g |
| Cholesterol | 3.5 g |
| Tween 40 (1.5% solution in water) | 75 ml |

The preformed vesicles were then mixed with an excess of a water immiscible material by placing the vesicles in one syringe, an excess of the water immiscible material which was to act as the cargo in a second syringe, and the syringes are joined through a three-way stopcock. The solutions were mixed from one syringe to the other for approximately 40–50 strokes at ambient temperature. The resulting solution was then centrifuged at 3500 RPM for 30 minutes to separate the unencapsulated water immiscible material from the lipid vesicles. Table 2 lists the water immiscible material uptake for a variety of different water immiscible materials. All values are in ml of water immiscible material/ml vesicle.

TABLE 2

| Mineral Oil | 1.0 ml/ml |
|---|---|
| Butyl Cellosolve | 0.11 ml/ml |
| Mineral Spirits | 0.18 ml/ml |
| Isodecyl Benzoate | 1.0 ml/ml |
| Tricresyl Phosphate | 1.0 ml/ml |

As can be seen, a large number of different materials can be incorporated at high concentration using this "cold-loading" procedure.

EXAMPLE 2

In this Example, a different wall forming material, polyoxyethylene 2 stearyl alcohol, and a different indifferent surfactant, sodium dodecyl sulphate (SDS), were used to form the vesicles. The amounts used to preform the vesicles are shown in Table 3.

TABLE 3

| POE (2) Stearyl Alcohol | 5.9 g |
|---|---|
| Cholesterol | 2.1 g |
| 1.5% SDS in Water | 41.5 ml |

The vesicles were formed in the same manner as described in connection with Example 1. The vesicles were then mixed with an excess of mineral oil (Drakeol #19) using the same syringe procedure as previously described and the oil-filled vesicles were separated by centrifugation. The uptake of mineral oil into the vesicles was greater than 0.7 ml oil/ml vesicle.

EXAMPLE 3

In this Example, a phospholipid, lecithin, was used to form the vesicles. The lecithin was dissolved in soybean oil, heated until a clear solution was formed, and then mixed with an excess of water, using the procedure described in Example 1, to form paucilamellar lipid vesicles. Table 4 shows the amounts of the different components used to form the vesicles. The vesicles included some oil in the aqueous center.

TABLE 4

| Lecithin (98%, Emulpur N-P1 Lucas Meyer, Inc.) | 6.4 g |
|---|---|
| Soybean Oil | 6.4 ml |
| Water | 26.0 ml |

The preformed phospholipid paucilamellar lipid vesicles were then mixed with an excess of additional soybean oil using the syringe technique previously described and centrifuged at 3500 RPM for 30 minutes. The uptake of the soybean oil in the second processing step was approximately 1 ml oil/ml vesicle. The same procedure has also been used with a 33% solution of cholesterol oleate in soybean oil being incorporated into the vesicles. The uptake was at least 0.67 ml/ml vesicle.

EXAMPLE 4

In this Example, additional oil was incorporated into the amorphous center of nonionic lipid vesicles which already had a small amount of oil therein. The procedures used were the same as those described in connection with Example 1 except mineral oil was incorporated into the heated lipid solution used to form the initial vesicles. Table 5 gives the ingredients used to preform the vesicles.

TABLE 5

| POE (9) Glycerol Monostearate | 20.3 g |
|---|---|
| Cholesterol | 3.5 g |
| Mineral Oil (Drakeol #19) | 25.0 ml |
| 1.5% SDS in Water | 75.0 ml |

After the vesicles were formed, they were mixed using the syringe method with additional mineral oil and centrifuged at 3500 RPM for 15 minutes to separate the vesicles from the oil. Uptake of additional mineral oil was approximately 0.7 ml mineral oil/ml vesicle.

EXAMPLE 5

In this Example, the uptake of DEET (diethyltoluamide) into negatively charged vessels was tested. DEET interferes with vesicle forming using a "hot-loading" technique, so insufficient amounts of DEET can be incorporated into vesicles using the "hot-loading" procedure. Negatively charged vesicles were formed using the same procedures as described in Example 1, using the materials shown in Table 6.

TABLE 6

| POE (9) Glycerol Monostearate | 11.2 g |
|---|---|
| Cholesterol | 1.9 g |
| Oleic Acid | 0.2 g |
| Tween 40 | 0.9 ml |
| Water | 42.0 ml |

The preformed negatively charged vesicles were then mixed with an excess of DEET and centrifuged at 3500 RPM for 30 minutes. Uptake of DEET into the vesicles was approximately 0.4 ml DEET/ml vesicle.

Similar results have been obtained with a variety of flavor oils, fragrances, and the hand cleaner d-limonene. In addition, the 40-50 strokes of the syringe, mixing the vesicles and the water immiscible material, has been replaced by merely placing all the materials in a tube and blending with a vortex mixer, stirrer, or homogenizer thereby encapsulating the water immiscible material Those skilled in the art may appreciate other methods which are within the scope of the present invention. Such other methods are included within the following claims.

What is claimed is:

1. A method of forming a paucilamellar lipid vesicle having a substantially oil-filled amorphous central cavity comprising the steps of:
   preforming a paucilamellar lipid vesicle having an aqueous material in the amorphous central cavity;
   mixing said preformed paucilamellar lipid vesicle with a water immiscible material to be incorporated into said central cavity under mixing conditions such that said water immiscible material is incorporated into said preformed vesicle; and
   separating said paucilamellar lipid vesicle from any of said water immiscible material not incorporated into said central cavity,
   whereby said amorphous central cavity of said paucilamellar lipid vesicle is substantially filled with said water immiscible material.

2. The method of claim 1 wherein an indifferent surfactant is provided in addition to the lipid used to form said vesicle.

3. The method of claim 2 wherein said indifferent surfactant is water-soluble.

4. The method of claim 3 wherein said water-soluble indifferent surfactant is selected from a group consisting of polyoxyethylene sorbitan esters, sodium dodecyl sulphate, $C_{12}$–$C_{18}$ fatty acids, and salts and mixtures thereof.

5. The method of claim 2 wherein said indifferent surfactant is not water soluble.

6. The method of claim 1 wherein said water immiscible material to be incorporated in said amorphous central cavity is volatile or heat labile at the temperatures used to preform said paucilamellar lipid vesicle.

7. The method of claim 6 wherein said water immiscible material is selected from a group consisting of diethyltoluamide, flavor oils, fragrance oils, d-limonene, water immiscible solvents, and mixtures thereof.

8. The method of claim 1 wherein said paucilamellar lipid vesicles have a non-ionic lipid as the primary bilayer-forming material.

9. The method of claim 1 wherein said paucilamellar lipid vesicles have a phospholipid as the primary bilayer-forming material.

10. The method of claim 1 wherein said preformed paucilamellar lipid vesicle contains oil in addition to said aqueous material in said amorphous central cavity.

* * * * *